(12) United States Patent
Tsuzuki (10) Patent No.: US 12,207,841 B2
(45) Date of Patent: Jan. 28, 2025

(54) ULTRASONIC PROBE AND PUNCTURE ADAPTER FOR ULTRASONIC PROBE

(71) Applicant: CANON MEDICAL SYSTEMS CORPORATION, Otawara (JP)

(72) Inventor: Kentaro Tsuzuki, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/865,579

(22) Filed: Jul. 15, 2022

(65) Prior Publication Data

US 2023/0015108 A1   Jan. 19, 2023

(30) Foreign Application Priority Data

Jul. 16, 2021   (JP) .................................. 2021-117923

(51) Int. Cl.
*A61B 17/34* (2006.01)
*A61B 8/00* (2006.01)

(52) U.S. Cl.
CPC ........ *A61B 17/3403* (2013.01); *A61B 8/4444* (2013.01); *A61B 2017/3405* (2013.01); *A61B 2017/3413* (2013.01)

(58) Field of Classification Search
CPC .............. A61B 17/3403; A61B 8/4444; A61B 17/3478; A61B 2090/3784; A61B 2017/3405–3413

See application file for complete search history.

(56) References Cited

U.S. PATENT DOCUMENTS

| | | | | |
|---|---|---|---|---|
| 2006/0241489 A1* | 10/2006 | Hiki | ..................... | A61B 8/0841 600/471 |
| 2015/0112200 A1* | 4/2015 | Oberg | .................. | A61B 8/4455 600/461 |
| 2017/0065250 A1* | 3/2017 | Sasady | .................... | A61B 8/085 |
| 2021/0045850 A1* | 2/2021 | Yu | ........................ | A61C 8/0089 |
| 2022/0079619 A1* | 3/2022 | Moskowitz | ........ | A61B 17/3403 |

FOREIGN PATENT DOCUMENTS

| | | | |
|---|---|---|---|
| JP | 03-041414 U | | 4/1991 |
| JP | 2001-178728 A | | 7/2001 |
| JP | 2006-271874 A | | 10/2006 |
| JP | 4755745 B2 | * | 8/2011 |

* cited by examiner

*Primary Examiner* — Patricia J Park
(74) *Attorney, Agent, or Firm* — Oblon, McClelland, Maier & Neustadt, L.L.P.

(57) ABSTRACT

An ultrasonic probe of an embodiment includes a head part. The head part includes a plurality of ultrasonic elements that output ultrasonic waves and receive reflected waves of the output ultrasonic waves. The head part is provided with a through hole for guiding a puncture needle and a slit for guiding the puncture needle to the through hole.

14 Claims, 4 Drawing Sheets

ULTRASONIC PROBE AND PUNCTURE ADAPTER FOR ULTRASONIC PROBE

CROSS-REFERENCE TO RELATED APPLICATION

The present application claims priority based on Japanese Patent Application No. 2021-117923 filed Jul. 16, 2021, the content of which is incorporated herein by reference.

FIELD

Embodiments disclosed in the present description and drawings relate to an ultrasonic probe and a puncture adapter for the ultrasonic probe.

BACKGROUND

Laparoscopic surgery is performed by making multiple small holes around a surgical site and inserting a surgical instrument and a diagnostic instrument such as an ultrasonic probe into the body through a tubular member called a trocar. The tip of the ultrasonic probe used in laparoscopic surgery is provided with, for example, a puncture guide (puncture hole or groove), and an organ can be punctured at an arbitrary angle by passing a puncture needle through the puncture guide.

In laparoscopic surgery, generally, an ultrasonic probe is inserted into the body from a trocar and a puncture needle is punctured directly from the body surface to access a puncture guide provided on the ultrasonic probe. However, the puncture guide is located behind the skin of a subject, which is difficult for an operator to visually recognize directly. Accordingly, when the puncture guide is a hole, for example, it is not easy to insert a puncture needle inserted from the body surface into a small hole (puncture guide). When the puncture guide is a groove, the puncture needle can be moved from the side to access the puncture guide even if the puncture needle inserted from the body surface does not come into contact with the puncture guide. However, since the puncture guide, which is a groove, has a wide opening on the side, the puncture needle easily falls off from the puncture guide during guiding. Accordingly, it is difficult to improve the operability of the puncture needle.

DETAILED DESCRIPTION

Hereinafter, ultrasonic probes and puncture adapters of the ultrasonic probes of embodiments will be described with reference to the drawings.

An ultrasonic probe of an embodiment includes a head part. The head part includes a plurality of ultrasonic elements that output ultrasonic waves and receive reflected waves of the output ultrasonic waves. The head part is provided with a through hole for guiding a puncture needle and a slit for guiding the puncture needle to the through hole.

First Embodiment

Figure 1:
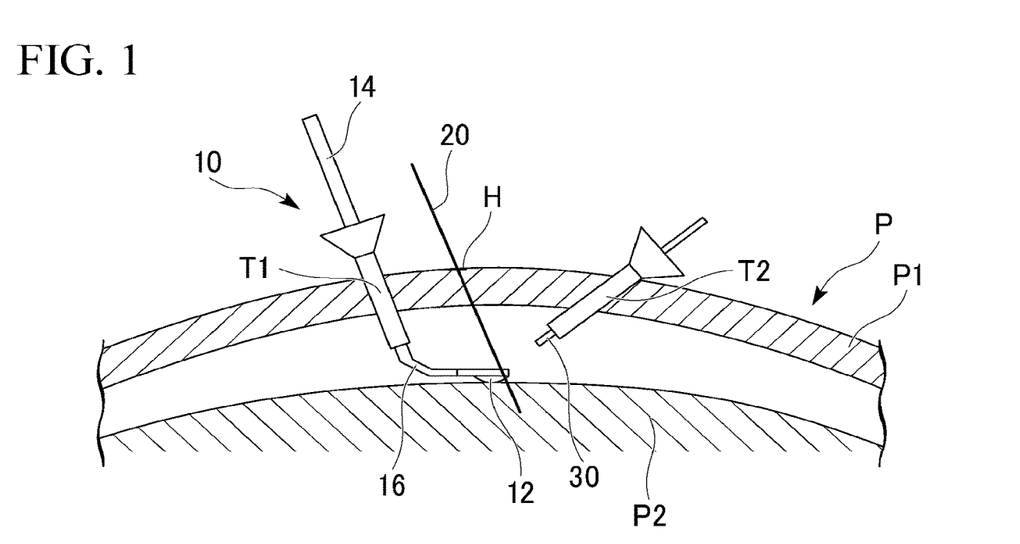
FIG. 1 is a diagram showing an example of a configuration of an ultrasonic probe 10 of a first embodiment.

FIG. 1 is a diagram showing an example of a configuration of an ultrasonic probe 10 of a first embodiment. The ultrasonic probe 10 is used, for example, in laparoscopic surgery (hereinafter referred to as a surgery). The surgery is performed using, for example, the ultrasonic probe 10, a puncture needle 20, an endoscope 30, a first trocar T1 and a second trocar T2.

While the surgery is being performed, the first trocar T1 and the second trocar T2 form a passage inside and outside a subject P. The ultrasonic probe 10 is introduced into the body of the subject P through the first trocar T1. The endoscope 30 is introduced into the body of the subject P through the second trocar T2. The puncture needle 20 is inserted into the skin P1 of the subject P. On the body surface of the subject P, for example, a body surface insertion point H into which the puncture needle 20 is inserted is indicated.

The ultrasonic probe 10 includes, for example, a transmission/reception head 12, a support part 14, and a bent part 16. The ultrasonic probe 10 is used, for example, to acquire an ultrasonic image of the inside of the body of the subject P in examination of the subject P. For example, an operator performs surgery while grasping the ultrasonic probe 10 with one hand and the puncture needle 20 with the other hand.

The transmission/reception head 12 is disposed, for example, between the skin P1 and an organ P2 of the subject P at the time of performing the surgery on the subject P. The transmission/reception head 12 includes a plurality of ultrasonic elements that output ultrasonic waves and receive reflected waves of the output ultrasonic waves. The plurality of ultrasonic elements are arranged in an array direction, transmit ultrasonic waves toward the organ P2, and receive reflected waves of the transmitted ultrasonic waves. The ultrasonic probe 10 transmits reflected wave information based on the received reflected waves of the ultrasonic waves to a control device or the like. The control device generates an ultrasonic image on the basis of the transmitted reflected wave information. The transmission/reception head 12 is an example of a head part.

The support part 14 is a long member having a small diameter. The bent part 16 is connected to the tip of the support part 14. The support part 14 is connected to the base end of the bent part 16 and the transmission/reception head 12 is connected to the tip of the bent part 16. The transmission/reception head 12 is attached to the tip of the support part 14 via the bent part 16. Since the bent part 16 is provided between the support part 14 and the transmission/ reception head 12, the transmission/reception head 12 can be provided along the surface of the organ P2. The length and shape of the support part 14 are arbitrary. Furthermore, other parts may be used to support the transmission/reception head 12 instead of using the support part 14.

The puncture needle 20 is a needle that is inserted into an internal organ from outside the body of the subject P in order to collect blood, body fluid, cells, and the like of the subject P. The endoscope 30 is a device having a small diameter and provided with a camera at the tip thereof. The endoscope 30 captures, for example, images of the transmission/reception head 12 of the ultrasonic probe 10 and the puncture needle 20. The endoscope 30 transmits an image captured by the camera to the control device. The control device displays, for example, an image transmitted by the endoscope 30 on a monitor or the like.

Figure 2:
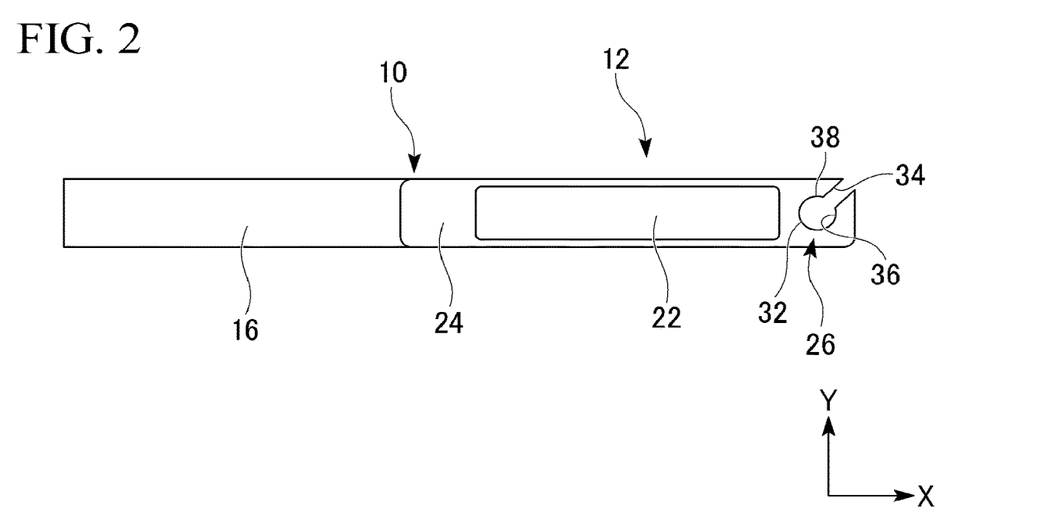
FIG. 2 is a plan view of a transmission/reception head 12.

FIG. 2 is a plan view of the transmission/reception head 12. The transmission/reception head 12 includes, for example, a transmission/reception unit 22, an outer frame part 24, and a puncture guide 26. The transmission/reception unit 22 includes, for example, a plurality of ultrasonic elements arranged in an array direction. The transmission/reception unit 22 outputs ultrasonic waves and receives reflected waves of the output ultrasonic waves. In FIG. 2, the X direction is the array direction and the Y direction is a lens direction. A direction orthogonal to the X direction and the Y direction is a transmission/reception direction. A direction along the transmission/reception direction may be referred to as a vertical direction, and a direction orthogonal to the transmission/reception direction may be referred to as a horizontal direction.

The shape of the transmission/reception head 12 viewed in the transmission/reception direction is a shape in which the four corners of a rectangle are chamfered. The transmission/reception unit 22 viewed in the transmission/reception direction has a rectangular shape. The longitudinal direction of the transmission/reception head 12 corresponds to the longitudinal direction of the transmission/reception unit 22, and the lateral direction of the transmission/reception head 12 corresponds to the lateral direction of the transmission/reception unit 22. The longitudinal direction of the transmission/reception head 12 and the transmission/reception unit 22 is along the array direction. The lateral direction of the transmission/reception head 12 and the transmission/reception unit 22 is along the lens direction.

The outer frame part 24 is provided to surround the outer periphery of the transmission/reception unit 22. The outer frame part 24 is connected to the bent part 16 and thus the transmission/reception head 12 is connected to the support part 14. The outer frame part 24 is provided with the puncture guide 26. The puncture guide 26 includes a through hole 32, a slit 34, an array direction wall 36, and a lens direction wall 38.

The through hole 32 is provided in the outer frame part 24 of the transmission/reception head 12. The through hole 32 is disposed in the array direction (longitudinal direction of the transmission/reception head 12 and the transmission/reception unit 22) from the transmission/reception unit 22 on the side opposite to the side on which the bent part 16 is positioned. The through hole 32 is a cylindrical hole portion that penetrates the outer frame part 24 in the transmission/reception direction. The puncture needle 20 penetrates the through hole 32. The through hole 32 guides the puncture needle 20 operated by the operator. Since the through hole 32 is disposed at a position extending from the transmission/reception unit 22 in the array direction, it is possible to facilitate long-axis puncture.

The shape of the through hole 32 viewed in the transmission/reception direction is approximately a C shape in which a part of a semicircular shape, for example, a position at an angle of 45° on the side far from the bent part 16 in each of the array direction and the lens direction of the through hole 32 is cut away. The shape of the through hole 32 viewed in the transmission/reception direction may be another shape. The shape of the through hole 32 viewed in the transmission/reception direction may be, for example, an oval shape, an elliptical shape, or a polygonal shape (regular polygonal shape) instead of a circular shape. The through hole 32 has a columnar shape having the same cross section in the transmission/reception direction. The through hole 32 may have a different shape in the transmission/reception direction. The through hole 32 may be cut at a position in a range forming an angle of any of 30° to 60° in each of the array direction and the lens direction of the through hole 32, for example.

The slit 34 is formed to extend from a cut position in the through hole 32 (a position forming an angle of 45° on the side far from the bent part 16 in each of the array direction and the lens direction of the through hole 32). The slit 34 viewed in the transmission/reception direction may extend to the outer edge of the transmission/reception head 12 in a direction other than the lens direction and the array direction of the ultrasonic elements provided in the transmission/reception head 12. The slit 34 guides the puncture needle 20 outside the through hole 32 to the through hole 32. The slit 34 may extend in other directions.

The slit 34 extends from the through hole 32 to the outer edge of the outer frame part 24 in the transmission/reception head 12 on the side away from the bent part 16 (support part 14) in a direction forming an angle of 45° with respect to each of the array direction and the lens direction. The width of the slit 34 viewed in the transmission/reception direction is substantially constant, and both sides of the slit 34 are linear. A part of the outer frame part 24 is divided by the slit 34, and the through hole 32 communicates with the outside of the outer frame part 24. The puncture needle 20 can be moved from the outside to the inside of the through hole 32 by moving along the horizontal plane.

Figure 3:
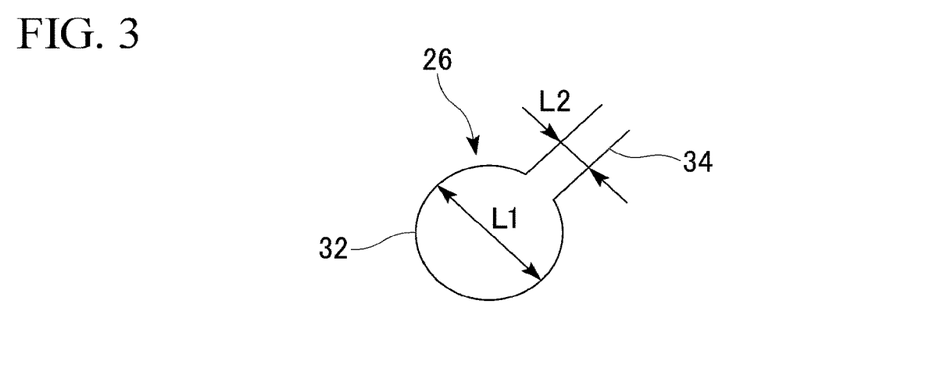
FIG. 3 is a diagram showing a relationship between the widths of a through hole 32 and a slit 34.

The relationship between the diameter of the through hole 32 and the notch width of the slit 34 is constant. FIG. 3 is a diagram showing the relationship between the widths of the through hole 32 and the slit 34. The notch width of the slit viewed in the transmission/reception direction is a length of ⅓ or less of the diameter L1 of the through hole 32. The diameter L1 of the through hole 32 and the notch width L2 of the slit 34 have the relationship of the following formula (1).

$$L1 > 3L2 \qquad (1)$$

Figure 4:
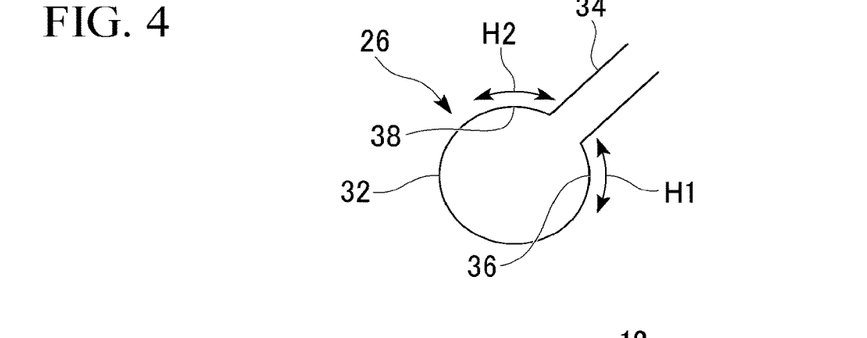
FIG. 4 is a diagram showing an array direction wall 36 and a lens direction wall 38.

The array direction wall 36 is composed of a surface on the array direction side from the center of the through hole 32. The lens direction wall 38 is composed of a surface on the lens direction side from the center of the through hole 32. FIG. 4 is a diagram showing the array direction wall 36 and the lens direction wall 38. The notch width of the slit 34 is less than ⅓ of the diameter of the through hole 32, and the width thereof is narrow. Accordingly, in the inner peripheral surface of the through hole 32, the surface on the array direction side from the center becomes the array direction wall 36 (a range indicated by a first arrow H1), and the surface on the lens direction side from the center becomes the lens direction wall 38 (a range indicated by a second arrow H2). The slit 34 is formed by cutting out a part of the through hole 32 within a range where the array direction wall 36 and the lens direction wall 38 can be left.

The ultrasonic probe 10 of the first embodiment includes the puncture guide 26, and the puncture guide 26 includes the through hole 32 and the slit 34. Since the puncture guide 26 includes the through hole 32, the operator can puncture an organ at an arbitrary angle with the puncture needle 20. The slit 34 is disposed at a position extending in a direction avoiding both the array direction and the lens direction. Accordingly, the operability of the puncture needle can be improved.

Further, the operator can perform puncturing with the puncture needle 20 attached to either the array direction wall 36 or the lens direction wall 38. Accordingly, the operator can apply the puncture needle 20 to the array direction wall 36 and adjust a puncture angle. The operator can reliably cause the ultrasonic probe 10 to capture a needle image by applying the puncture needle to the lens direction wall 38 to perform puncture.

Further, the width of the slit 34 is narrow and the length thereof is ⅓ or less of the diameter L1 of the circle when the through hole 32 is viewed in the circumferential direction. Accordingly, it becomes difficult for the puncture needle 20 to enter the slit 34 while the operator is operating the puncture needle 20, and thus the puncture needle 20 penetrating the through hole 32 can be prevented from falling out of the through hole 32 through the slit 34.

In particular, the puncture needle 20 operated by the operator is often moved in the array direction and thus, if an opening such as a slit is provided in the array direction, for example, the puncture needle 20 easily falls out of the through hole 32. In this respect, the array direction wall 36 is provided in the ultrasonic probe 10 of the first embodiment, and thus the puncture needle 20 can be suitably prevented from falling off.

Although the width of the slit 34 viewed in the transmission/reception direction is substantially constant in the first embodiment, the width of the slit 34 may vary. For example, both sides of the slit 34 viewed in the transmission/reception direction may be wavy, and the width of the slit 34 may vary depending on the position of the slit 34 in the extending direction. A dent or a protrusion may be formed at a position in the middle of the slit 34 in the longitudinal direction when viewed in the transmission/reception direction.

Second Embodiment

Figure 5:
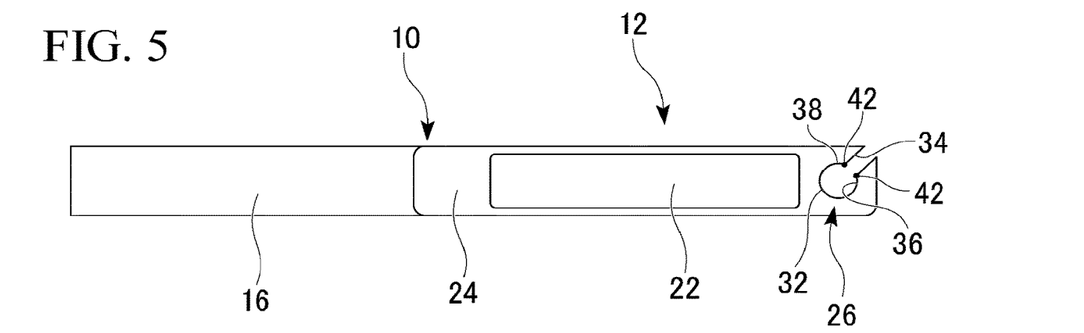
FIG. 5 is a diagram showing an example of a configuration of an ultrasonic probe 10 of a second embodiment.

Next, a second embodiment will be described. In the following description of the second and subsequent embodiments, elements and the like common to those of the first embodiment may be designated with the same numerals in the drawings and description thereof may be omitted. FIG. 5 is a diagram showing an example of a configuration of an ultrasonic probe 10 of the second embodiment. The ultrasonic probe 10 of the second embodiment is different from that of the first embodiment in that the puncture guide 26 includes a protrusion 42. Hereinafter, the ultrasonic probe 10 of the second embodiment will be described focusing on differences from the first embodiment.

Figure 6:
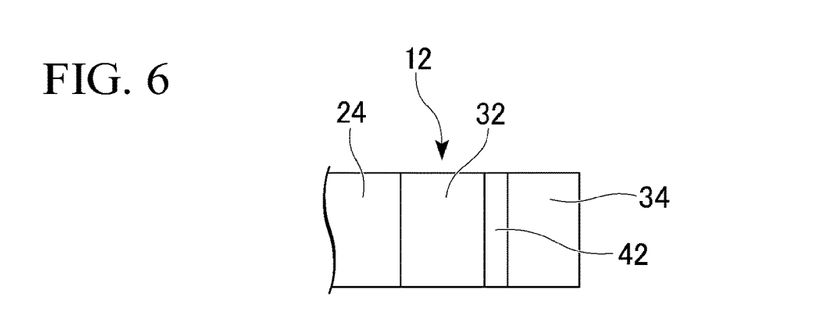
FIG. 6 is a side sectional view of the through hole 32.

The protrusion 42 included in the puncture guide 26 is formed to protrude toward the center of the through hole 32 in the vicinity of the extending portion of the slit 34 in the through hole 32. The protrusion 42 is provided on both of the two extending portions of the slit 34 in the through hole 32. FIG. 6 is a side sectional view of the through hole 32. The protrusion 42 is a pillar body along the depth direction of the through hole 32, more specifically, a columnar body. The protrusion 42 prevents the puncture needle 20 penetrating the through hole 32 from falling out through the slit 34. The protrusion 42 is an example of a projection. The protrusion 42 is an example of a falling prevention structure.

The ultrasonic probe 10 of the second embodiment has the same effect as that of the first embodiment. Further, the ultrasonic probe 10 of the second embodiment is provided with the protrusions 42 at the two extending portions of the slit 34 in the through hole 32. In a puncture operation performed by the operator passing the puncture needle 20 through the through hole 32, the puncture needle 20 may be moved in the horizontal direction.

At this time, since the slit 34 extends from the through hole 32 and reaches the outer edge of the outer frame part 24, there is a concern that the puncture needle 20 may fall out of the outer frame part 24 from the through hole 32 through the slit 34. In this respect, the protrusions 42 are provided at the extending portions of the slit 34 in the through hole 32, and thus the puncture needle 20 moving in the horizontal direction often comes into contact with the protrusions 42 before reaching the slit 34. Since the puncture needle 20 in contact with the protrusions 42 is hindered from moving in the horizontal direction before reaching the slit 34, the puncture needle 20 can be prevented from falling out of the outer frame part 24 through the slit 34.

Although the protrusion 42 has a cylindrical shape in the second embodiment, it may be a columnar body having a cross section other than a circular shape. Further, the protrusion 42 may have a shape other than the columnar body. The protrusion 42 may be spherical, for example. The protrusion 42, which is spherical or the like, may be disposed, for example, at the uppermost position (closest to the skin P1) of the inner surface of the through hole 32 in the transmission/reception direction. The protrusion 42 may be disposed at the lowest position (closest to the organ P2) in the through hole 32. The protrusion 42 may be disposed at an intermediate position in the through hole 32 in the transmission/reception direction. The protrusion 42 may be disposed at a plurality of positions in the through hole 32 in the depth direction.

Further, the falling prevention structure may be a structure other than the protrusion 42. The falling prevention structure may be, for example, a depression from the inner circumference of the through hole 32 viewed in the transmission/reception direction toward the direction away from the through hole 32. Although the falling prevention structure is provided at the two extending portions of the slit 34 in the through hole 32, it may be provided in only one thereof or may be provided in a portion other than the two extending portions of the slit 34 in the through hole 32.

Third Embodiment

Figure 7:
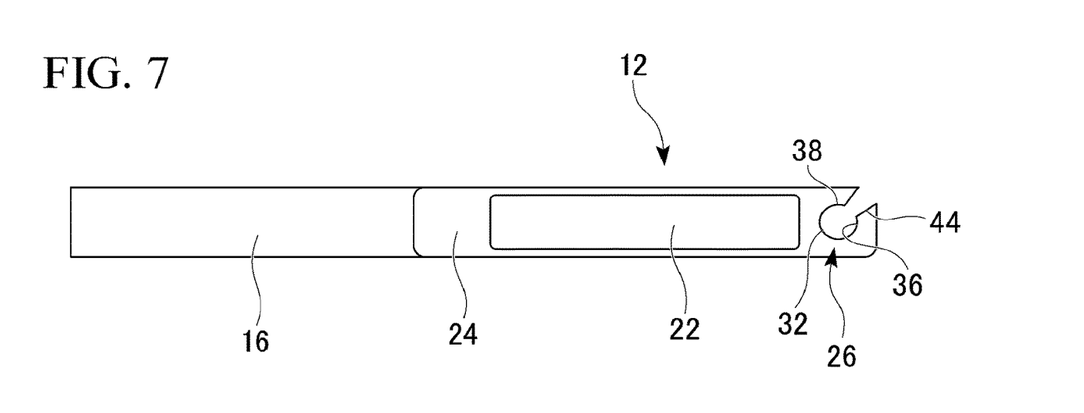
FIG. 7 is a diagram showing an example of a configuration of an ultrasonic probe 10 of a third embodiment.

Next, a third embodiment will be described. FIG. 7 is a diagram showing an example of a configuration of an ultrasonic probe 10 of the third embodiment. The ultrasonic probe 10 of the third embodiment is mainly different from the first embodiment with respect to the shape of a slit 44 in the puncture guide 26. The width of the slit 34 viewed in the transmission/reception direction in the first embodiment is substantially constant, whereas the width of the slit 44 viewed in the transmission/reception direction in the third embodiment becomes narrower as it becomes closer to the through hole 32 and thus becomes narrower as it becomes closer to the outer edge of the outer frame part 24. Accordingly, the width of the slit 44 on the outer edge side of the outer frame part 24 of the transmission/reception head 12 in the transmission/reception direction is wider than the width thereof on the side of the through hole 32.

The ultrasonic probe 10 of the third embodiment has the same effect as that of the first embodiment. Further, in the ultrasonic probe 10 of the third embodiment, the width of the slit 44 viewed in the transmission/reception direction is the narrowest at the end portion on the side of the through hole 32 and the widest at the end portion on the outer edge side of the outer frame part 24. Accordingly, the puncture needle 20 penetrating the through hole 32 is less likely to fall out of the through hole 32, and the puncture needle 20 positioned outside the transmission/reception head 12 can be easily guided to the through hole 32 through the slit 44.

Fourth Embodiment

Figure 8:
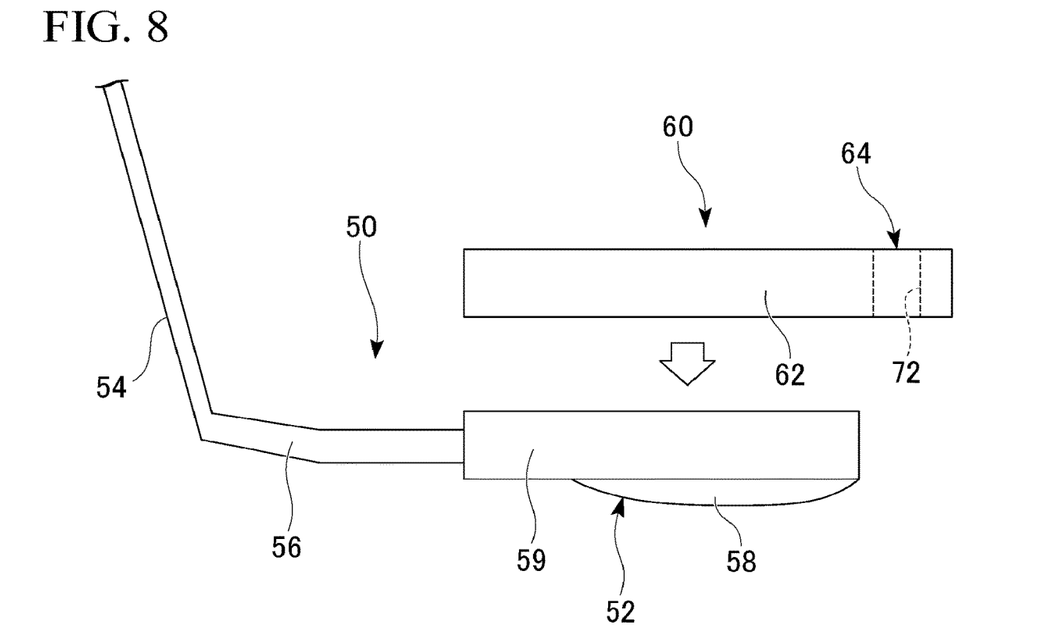
FIG. 8 is an exploded view of an ultrasonic probe 50 and a puncture adapter 60.
Figure 9:
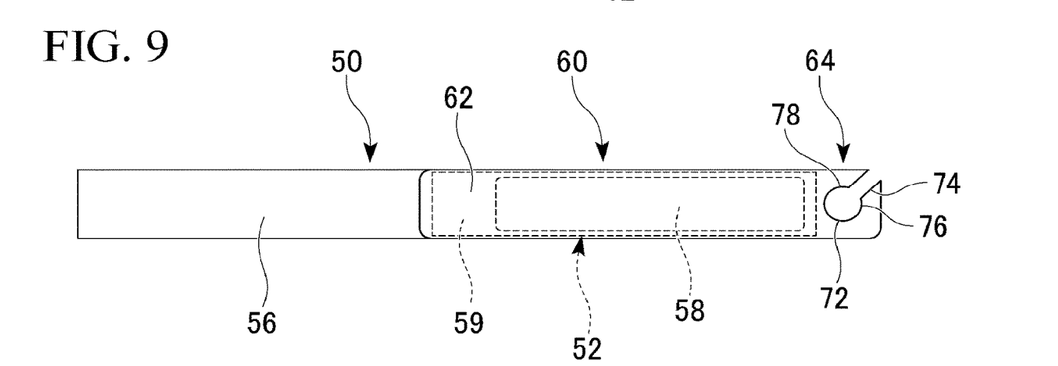
FIG. 9 is a plan view of the ultrasonic probe 50 to which the puncture adapter 60 is attached.

Next, a fourth embodiment will be described. FIG. 8 is a diagram showing an example of a configuration of an ultrasonic probe 50 according to the fourth embodiment. FIG. 9 is a plan view of a puncture adapter of the ultrasonic probe 50 to which the puncture adapter 60 is attached. The ultrasonic probe 50 of the fourth embodiment includes a transmission/reception head 52, a support part 54, and a bent part 56. Thereamong, the support part 54 and the bent part 56 have the same configurations as those of the ultrasonic probe 10 of the first embodiment.

The transmission/reception head 52 includes a transmission/reception unit 58 and an outer frame part 59. The transmission/reception unit 58 has the same configuration as the transmission/reception unit 22 of the first embodiment. The outer frame part 59 is thinner than the outer frame part 24 of the first embodiment, and the size thereof viewed in the transmission/reception direction is smaller than that of the outer frame part 24 of the first embodiment. The outer frame part 24 of the first embodiment is provided with the puncture guide 26, whereas the outer frame part 59 is not provided with the puncture guide.

The puncture adapter 60 is attached to the transmission/reception head 52 of the ultrasonic probe 50. The puncture adapter 60 includes, for example, a mounting part 62 and a puncture guide 64. The mounting part 62 is mounted to cover the transmission/reception head 52. The puncture guide 64 is provided on the mounting part 62. The puncture guide 64 includes a through hole 72, a slit 74, an array direction wall 76, and a lens direction wall 78. The through hole 72, the slit 74, the array direction wall 76, and the lens direction wall 78 of the puncture guide 64 have the same configurations as those of the through hole 32, the slit 34, the array direction wall 36, and the lens direction wall 38 of the puncture guide 26 in the first embodiment.

The ultrasonic probe 50 of the fourth embodiment has the same effect as that of the ultrasonic probe 10 of the first embodiment according to the puncture adapter 60 attached thereto. Further, by providing the puncture guide 64 in the puncture adapter 60, the operability of the puncture needle can be improved even in an ultrasonic probe that does not include a puncture guide. Although the puncture adapter 60 is attached to an ultrasonic probe that is not provided with a puncture guide, it may be attached to an ultrasonic probe provided with a puncture guide. Further, by attaching the puncture adapter to an ultrasonic probe, a puncture guide may be configured by the ultrasonic probe and the puncture adapter.

Modified Example 1

Figure 10A:
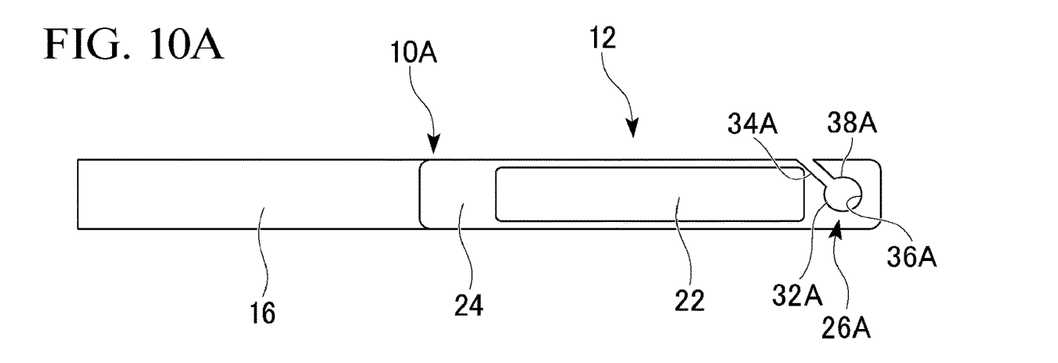
FIG. 10A is a plan view of an ultrasonic probe 10A of modified example 1.

Next, modified example 1 will be described. FIG. 10A is a plan view of an ultrasonic probe 10A of modified example 1. The ultrasonic probe 10A of the first modified example includes a puncture guide 26A. The puncture guide 26A includes a through hole 32A, a slit 34A, an array direction wall 36A, and a lens direction wall 38A.

The through hole 32A is disposed at a position in the array direction opposite to the side on which the bent part 16 is located from the transmission/reception unit 22 in the outer frame part 24 in the transmission/reception head 12. The through hole 32A viewed in the transmission/reception direction has a substantially C shape in which a part of a substantially circular shape is cut out, and penetrates the outer frame part 24 in the transmission/reception direction.

The slit 34A is formed by cutting out a position of the through hole 32A forming an angle of 45° on the side close to the bent part 16 in each of the array direction and the lens direction. The slit 34A viewed in the transmission/reception direction extends from the through hole 32A to the outer edge of the outer frame part 24 in the transmission/reception head 12 in a direction forming an angle of 45° on the side close to the bent part 16 in each of the array direction and the lens direction. In this manner, even if the puncture guide 26A is formed such that the slit 34A extends toward the bent part 16, the operability of the puncture needle can be improved as in the first embodiment.

Modified Example 2

Figure 10B:
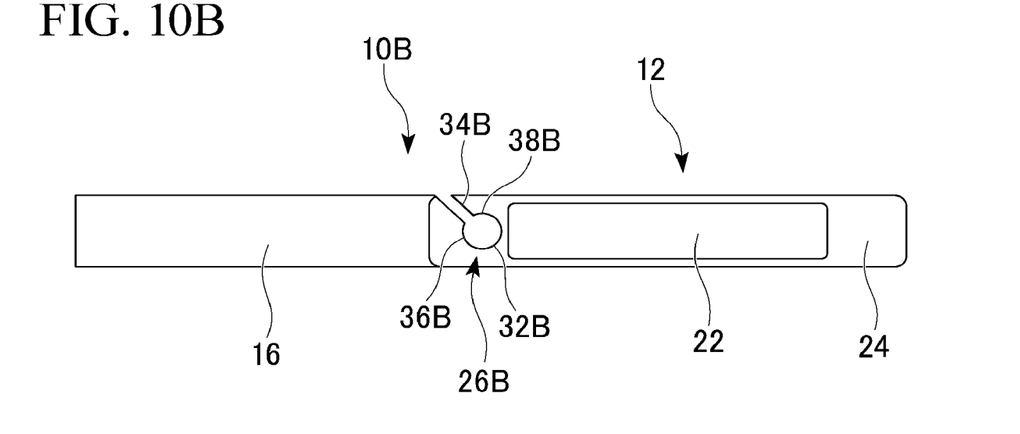
FIG. 10B is a plan view of an ultrasonic probe 10B of modified example 2.

Next, modified example 2 will be described. FIG. 10B is a plan view of an ultrasonic probe 10B of modified example 2. The ultrasonic probe 10B of modified example 2 includes a puncture guide 26B. The puncture guide 26B includes a through hole 32B, a slit 34B, an array direction wall 36B, and a lens direction wall 38B.

The through hole 32B is disposed at a position in the array direction on the side where the bent part 16 is located from the transmission/reception unit 22 in the outer frame part 24 in the transmission/reception head 12. The through hole 32B viewed in the transmission/reception direction has a substantially C shape in which a part of a substantially circular shape is cut out, and penetrates the outer frame part 24 in the transmission/reception direction.

The slit 34B is formed by cutting out a position of the through hole 32B forming an angle of 45° on the side close to the bent part 16 in each of the array direction and the lens direction. The slit 34B viewed in the transmission/reception direction extends from the through hole 32B to the outer edge of the outer frame part 24 in the transmission/reception head 12 in a direction forming an angle of 45° on the side close to the bent part 16 in each of the array direction and the lens direction. In this manner, even if the puncture guide 26B is formed such that the slit 34B extends toward the bent part 16, the operability of the puncture needle can be improved as in the first embodiment.

Modified Example 3

Figure 10C:
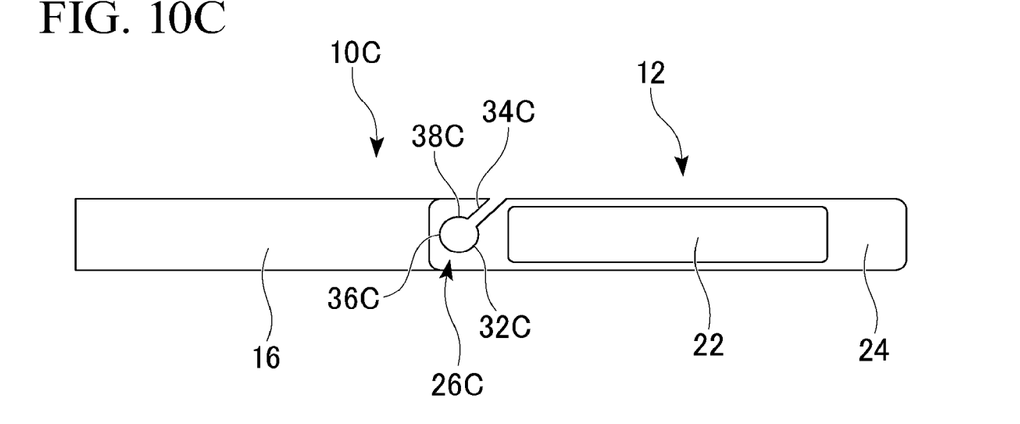
FIG. 10C is a plan view of an ultrasonic probe 10C of modified example 3.

Next, modified example 3 will be described. FIG. 10C is a plan view of an ultrasonic probe 10C of modified example 3. The ultrasonic probe 10C of the modified example 3 includes a puncture guide 26C. The puncture guide 26C includes a through hole 32C, a slit 34C, an array direction wall 36C, and a lens direction wall 38C.

The through hole 32C is disposed at a position in the array direction on the side where the bent part 16 is located from the transmission/reception unit 22 in the outer frame part 24 in the transmission/reception head 12. The through hole 32C viewed in the transmission/reception direction has a substantially C shape in which a part of a substantially circular shape is cut out, and penetrates the outer frame part 24 in the transmission/reception direction.

The slit 34C is formed by cutting out a position of the through hole 32C forming an angle of 45° on the side far from the bent part 16 in each of the array direction and the lens direction. The slit 34C viewed in the transmission/reception direction extends from the through hole 32C to the outer edge of the outer frame part 24 in the transmission/reception head 12 in a direction forming an angle of 45° on the side far from the bent part 16 in each of the array direction and the lens direction. In this manner, even if the puncture guide 26C is formed such that the slit 34C extends toward the bent part 16, the operability of the puncture needle can be improved as in the first embodiment.

Modified Example 4

Figure 11:
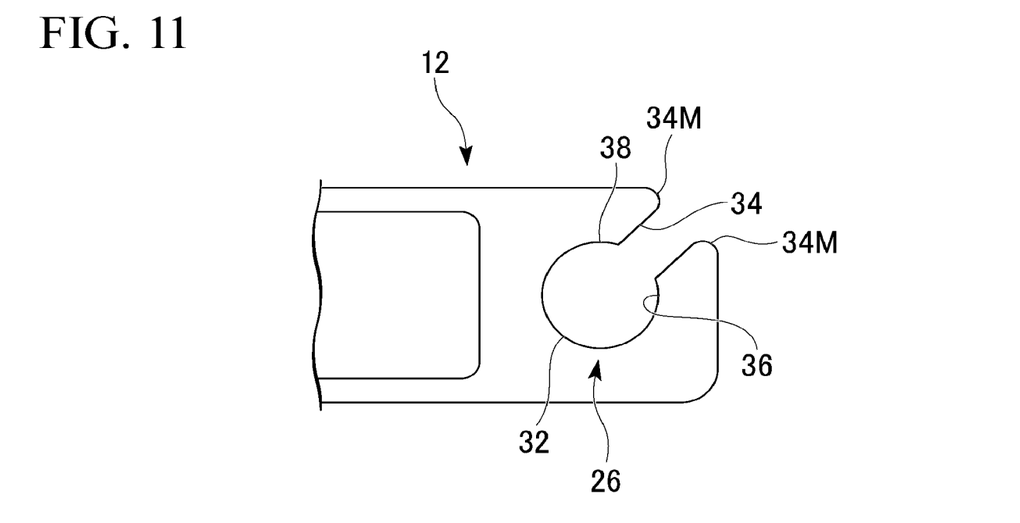
FIG. 11 is an enlarged view of the tip of a transmission/reception head 12 in an ultrasonic probe of modified example 4.

Next, modified example 4 will be described. FIG. 11 is an enlarged view of the tip of a transmission/reception head 12 in an ultrasonic probe of modified example 4. The same puncture guide 26 as that of the first embodiment is provided at the tip of the transmission/reception head 12 of the ultrasonic probe of modified example 4. The puncture guide 26 includes a through hole 32, a slit 34, an array direction wall 36, and a lens direction wall 38. The transmission/reception head 12 in the ultrasonic probe of modified example 4 is mainly different from the first embodiment with respect to the shape of the entrance/exit portion of the slit 34.

The outer entrance/exit portion of the slit 34 of the first embodiment has a sharp shape, whereas the outer entrance/exit portion 34M of the slit 34 of modified example 4 is chamfered into an arc shape. The shape of the outer entrance/exit portion 34M is a curved shape and may be a shape other than an arc shape as long as it does not include a sharp portion. The shape of the outer entrance/exit portion 34M may be, for example, a semicircular shape, a curved shape other than a circular shape, a wavy shape, or the like.

In the puncture guide 26 of modified example 4, since the outer entrance/exit portion 34M has a chamfered arc shape, the puncture needle 20 penetrating the through hole 32 is less likely to fall out of the through hole 32, and the puncture needle 20 positioned outside the transmission/reception head 12 can be easily guided to the through hole 32 through the slit 34. Further, since the outer entrance/exit portion 34M has a chamfered arc shape, it is possible to prevent the inside of the body of a patient from being injured by the corner of the outer entrance/exit portion 34M. The shape of the outer entrance/exit portion 34M is a curved shape and may be a shape other than an arc shape as long as it does not include a sharp portion.

According to at least one of the embodiments described above, the head part including a plurality of ultrasonic elements that output ultrasonic waves and receive reflected waves of the output ultrasonic waves, and a long support part to which the head part is attached are included, wherein the head part is provided with the through hole for guiding the puncture needle and a slit for guiding the puncture needle to the through hole, and the slit extends to the outer edge of the head part in a direction other than the lens direction and the array direction of the ultrasonic elements, and thus the operability of the puncture needle can be improved.

Although several embodiments have been described, these embodiments are presented as examples and are not intended to limit the scope of the invention. These embodiments can be implemented in various other embodiments, and various omissions, replacements, and changes can be made without departing from the gist of the invention. These embodiments and modifications thereof are included in the scope of the invention described in the claims and the equivalent scope thereof, as are included in the scope and gist of the invention.

With respect to the above-described embodiments, the following appendices are disclosed as one aspect and selective features of the invention.

(Appendix 1)

An ultrasonic probe including:
a head part including a plurality of ultrasonic elements that output ultrasonic waves and receive reflected waves of the output ultrasonic waves; and
a long support part to which the head part is attached,
wherein the head part is provided with a through hole for guiding a puncture needle and a slit for guiding the puncture needle to the through hole, and
the slit extends to an outer edge of the head part in a direction other than a lens direction and an array direction of the ultrasonic elements.

(Appendix 2)

The notch width of the slit may be ⅓ or less of the diameter of the through hole.

(Appendix 3)

A falling prevention structure that prevents falling of the puncture needle penetrating the through hole through the slit may be further included.

(Appendix 4)

The falling prevention structure may be a protrusion protruding from the inner circumference of the through hole toward the center of the through hole.

(Appendix 5)

The falling prevention structure may be a depression from the inner circumference of the through hole toward a direction away from the center of the through hole.

(Appendix 6)

The protrusion may be a columnar body along the depth direction of the through hole.

(Appendix 7)

The slit may be provided on at least one of the support part side and the opposite side to the support part side when viewed from an arrangement position of the ultrasonic elements in the head part.

(Appendix 8)

The width of the slit on the side of the outer edge of the head part may be wider than the width on the side of the through hole.

(Appendix 9)

The slit may extend from the through hole to the outer edge of the head part in a direction away from the support part.

(Appendix 10)

An outer entrance/exit portion of the slit may have a chamfered curved shape.

(Appendix 11)

A puncture adapter for an ultrasonic probe attached to a head part including a plurality of ultrasonic elements that output ultrasonic waves and receive reflected waves of the output ultrasonic waves, and provided with a through hole for guiding a puncture needle and a slit for guiding the puncture needle to the through hole,
wherein the slit extends to the outer edge in a direction other than a lens direction and an array direction of the ultrasonic elements in a state in which the puncture adapter is attached to the ultrasonic probe.

What is claimed is:

1. An ultrasonic probe, comprising:
a head part including a plurality of ultrasonic elements that output ultrasonic waves and receive reflected waves of the output ultrasonic waves; and
a long support part to which the head part is attached,
wherein the head part is provided with a through hole for guiding a puncture needle and a slit for guiding the puncture needle to the through hole,
the head part of the ultrasonic probe is insertable into a body of a subject, and
the slit is provided on a side opposite to the long support part side with respect to a position of the ultrasonic elements in the head part.

2. The ultrasonic probe according to claim 1, wherein the slit extends from the through hole to an outer edge of the head part.

3. The ultrasonic probe according to claim 1, wherein the slit extends to an outer edge of the head part in a direction other than a lens direction and an array direction of the ultrasonic elements.

4. The ultrasonic probe according to claim 1, wherein the slit extends to an outer edge of the head part toward a predetermined angle with respect to a lens direction or an array direction of the ultrasonic elements.

5. The ultrasonic probe according to claim 1, wherein a notch width of the slit is equal to or less than D/3, wherein D is a diameter of the through hole.

6. The ultrasonic probe according to claim 1, further comprising a falling prevention structure that prevents falling of the puncture needle penetrating the through hole through the slit.

7. The ultrasonic probe according to claim 6, wherein the falling prevention structure is a protrusion protruding from an inner circumference of the through hole toward a center of the through hole.

8. The ultrasonic probe according to claim 7, wherein the protrusion is a columnar body along a depth direction of the through hole.

9. The ultrasonic probe according to claim 6, wherein the falling prevention structure is a depression from an inner circumference of the through hole toward a direction away from a center of the through hole.

10. The ultrasonic probe according to claim 1, wherein the slit extends from the through hole to an outer edge of the head part in a direction away from the long support part.

11. The ultrasonic probe according to claim 1, wherein an outer entrance/exit portion of the slit has a chamfered curved shape.

12. The ultrasonic probe according to claim 1, wherein a width of the slit on a side of an outer edge of the head part is wider than a width on a side of the through hole.

13. The ultrasonic probe according to claim 1, wherein the head part is attached to a tip of the long support part.

14. The ultrasonic probe according to claim 1, wherein the head part is attached to a tip of the long support part via a bent part.

* * * * *